(12) United States Patent  (10) Patent No.: US 7,447,558 B2
Pratt  (45) Date of Patent: Nov. 4, 2008

(54) APPARATUS FOR DETERMINING A THREE DIMENSIONAL SHAPE OF AN OBJECT

(75) Inventor: Gregory C. Pratt, Boca Raton, FL (US)

(73) Assignee: The Ohio Willow Wood Company, Mt. Sterling, OH (US)

( * ) Notice: Subject to any disclaimer, the term of this patent is extended or adjusted under 35 U.S.C. 154(b) by 137 days.

(21) Appl. No.: 11/228,697

(22) Filed: Sep. 16, 2005

(65) Prior Publication Data

US 2006/0062449 A1   Mar. 23, 2006

Related U.S. Application Data

(60) Provisional application No. 60/611,364, filed on Sep. 18, 2004.

(51) Int. Cl.
*G06F 19/00* (2006.01)
*G06K 9/00* (2006.01)

(52) U.S. Cl. .................. 700/118; 382/154; 600/587; 623/901

(58) Field of Classification Search .......... 700/11, 700/99, 120, 98, 182, 163, 167; 356/601; 702/153; 382/128; 33/515
See application file for complete search history.

(56) References Cited

U.S. PATENT DOCUMENTS

| | | | |
|---|---|---|---|
| 3,985,444 A | 10/1976 | Takashima et al. | 356/109 |
| 4,653,104 A | 3/1987 | Tamura | 382/1 |
| 4,745,290 A | 5/1988 | Frankel et al. | 250/560 |
| 4,773,029 A | 9/1988 | Claesson et al. | 364/562 |

(Continued)

FOREIGN PATENT DOCUMENTS

AT   363 580   8/1981

(Continued)

OTHER PUBLICATIONS

Lancaster, Jack L., et al., "Evaluation of a Laser Scanner for Shape Sensing BKN Amputees," pp. 155-156, RESNA 12th Annual Conference, New Orleans, Louisiana 1989.

(Continued)

*Primary Examiner*—Kidest Bahta
(74) *Attorney, Agent, or Firm*—Standley Law Group LLP

(57) ABSTRACT

An apparatus is described that uses cameras arranged on, in, or about a structure adapted to fit over, around, or about an object to be measured. Projectors are arranged on, in, or about the structure to project light toward the object. The projectors and/or the cameras may be electronically connected to a computer processor which controls their operation. A light pattern is projected onto the object to be measured while the cameras capture images of the object from several angles about the object. The data collected from the images taken of the pattern on the object may be used to form a mathematical three-dimensional data model of the object. The three-dimensional model may be displayed in digital form on a visual display device of a personal computer. The three-dimensional model of the object may be used in the manufacture of fitments or coverings for the object. In one example, the apparatus is used by a prosthetist to map the stump of an amputee to properly fit the amputee with a prosthetic device.

13 Claims, 14 Drawing Sheets

U.S. PATENT DOCUMENTS

| | | | | |
|---|---|---|---|---|
| 4,819,660 | A * | 4/1989 | Smith | 600/587 |
| 4,821,200 | A | 4/1989 | Oberg | 700/182 |
| 4,895,434 | A | 1/1990 | Stern et al. | 350/484 |
| 4,929,843 | A | 5/1990 | Chmielewski et al. | 250/561 |
| 4,969,106 | A | 11/1990 | Vogel et al. | 364/508 |
| 4,982,438 | A | 1/1991 | Usami et al. | 382/154 |
| 5,040,005 | A * | 8/1991 | Davidson et al. | 396/429 |
| 5,127,420 | A | 7/1992 | Horvath | 128/782 |
| 5,307,151 | A | 4/1994 | Hof et al. | 356/376 |
| 5,339,154 | A | 8/1994 | Gassler et al. | 356/604 |
| 5,360,446 | A | 11/1994 | Kennedy | 128/898 |
| 5,432,703 | A | 7/1995 | Clynch et al. | 700/163 |
| 5,448,472 | A | 9/1995 | Mushabac | 433/70 |
| 5,477,459 | A | 12/1995 | Clegg et al. | |
| 5,528,517 | A | 6/1996 | Løken | 364/560 |
| 5,539,649 | A | 7/1996 | Walsh et al. | 700/163 |
| 5,741,215 | A | 4/1998 | D'Urso | 600/407 |
| 5,742,068 | A | 4/1998 | Dybdahl et al. | 250/559.19 |
| 5,753,931 | A | 5/1998 | Borchers et al. | 250/559.22 |
| RE35,816 | E | 6/1998 | Schultz | 356/608 |
| 5,781,652 | A | 7/1998 | Pratt | 382/128 |
| 5,886,775 | A | 3/1999 | Houser et al. | 356/401 |
| 5,911,126 | A * | 6/1999 | Massen | 702/153 |
| 5,917,640 | A | 6/1999 | Staver | 359/216 |
| 5,969,823 | A | 10/1999 | Wurz et al. | 356/386 |
| 6,028,672 | A | 2/2000 | Geng | 356/602 |
| 6,075,605 | A | 6/2000 | Futamura et al. | 356/608 |
| 6,081,739 | A | 6/2000 | Lemchen | 600/407 |
| 6,144,386 | A | 11/2000 | Pratt | 345/848 |
| 6,177,999 | B1 | 1/2001 | Wurz et al. | 356/386 |
| 6,236,743 | B1 | 5/2001 | Pratt | 382/128 |
| 6,256,099 | B1 | 7/2001 | Kaufman et al. | 356/603 |
| 6,287,119 | B1 | 9/2001 | van Nifterick et al. | 433/213 |
| 6,326,994 | B1 | 12/2001 | Yoshimatsu | 348/46 |
| 6,369,899 | B1 | 4/2002 | Hamada | 356/603 |
| 6,383,148 | B1 | 5/2002 | Pusch et al. | 600/587 |
| 6,421,629 | B1 | 7/2002 | Ishiyama | 702/159 |
| 6,424,422 | B1 * | 7/2002 | Kamon et al. | 356/623 |
| 6,480,678 | B1 | 11/2002 | Matsushima | 396/155 |
| 6,490,541 | B1 | 12/2002 | Ariga et al. | 702/158 |
| 6,493,095 | B1 | 12/2002 | Song et al. | 356/603 |
| 6,512,844 | B2 | 1/2003 | Bouguet et al. | 382/154 |
| 6,542,249 | B1 * | 4/2003 | Kofman et al. | 356/601 |
| 6,542,250 | B1 | 4/2003 | Michaelis et al. | 356/601 |
| 6,549,289 | B1 | 4/2003 | Ellis | 356/603 |
| 6,564,086 | B2 | 5/2003 | Marchitto et al. | 600/425 |
| 6,590,573 | B1 * | 7/2003 | Geshwind | 345/419 |
| 6,674,893 | B1 | 1/2004 | Abe et al. | 382/154 |
| 6,829,377 | B2 * | 12/2004 | Milioto | 382/128 |
| 7,006,952 | B1 * | 2/2006 | Matsumoto et al. | 703/2 |
| 2002/0176608 | A1 | 11/2002 | Rose | 382/108 |
| 2003/0122954 | A1 | 7/2003 | Kassatly | 348/335 |
| 2003/0137510 | A1 | 7/2003 | Massen | 345/420 |
| 2003/0142863 | A1 | 7/2003 | Massen | 382/154 |
| 2004/0032595 | A1 | 2/2004 | Massen | 356/603 |
| 2004/0032649 | A1 | 2/2004 | Kondo et al. | 359/364 |
| 2007/0276224 | A1 * | 11/2007 | Lang et al. | 600/410 |

FOREIGN PATENT DOCUMENTS

| | | |
|---|---|---|
| DE | 2 250 679 | 4/1973 |
| DE | 4232606 A1 | 3/1994 |
| DE | 44 17 872 A1 | 11/1995 |
| DE | 595 04 229 D | 12/1998 |
| GB | 2 257 250 A | 1/1993 |
| WO | WO83/04114 | 11/1983 |
| WO | WO90/10194 | 9/1990 |
| WO | WO92/08175 | 5/1992 |
| WO | WO95/31934 | 11/1995 |

OTHER PUBLICATIONS

Carrico, Frank, "Rapid Anthropometry for CAD/CAM Design in Prosthetics and Orthotics," pp. 157-158, RESNA 12th Annual Conference, New Orleans, Louisiana, 1989.

Lancaster, Jack L., et al., "A Computerized System to Manufacture Prostheses for Amputees in Developing Countries," 15 pages, JPO, 1989; vol. 1, No. 3, p. 165.

Föhr, Ralph, Fortschritte der Robotik 7, "Photogrammetrische Erfassung Räumlicher Informationen Aus Videobildern," 6. Steroskopische Vermessungen von Raumpunkten, 1990. (Translated: Föhr, Ralph, Progress in Robotics, vol. 7, "Photogrammatic Inclusion of Spatial Information on Video Displays," Chapter 6, Stereoscopic Measurement of Points in Space, 1990.).

* cited by examiner

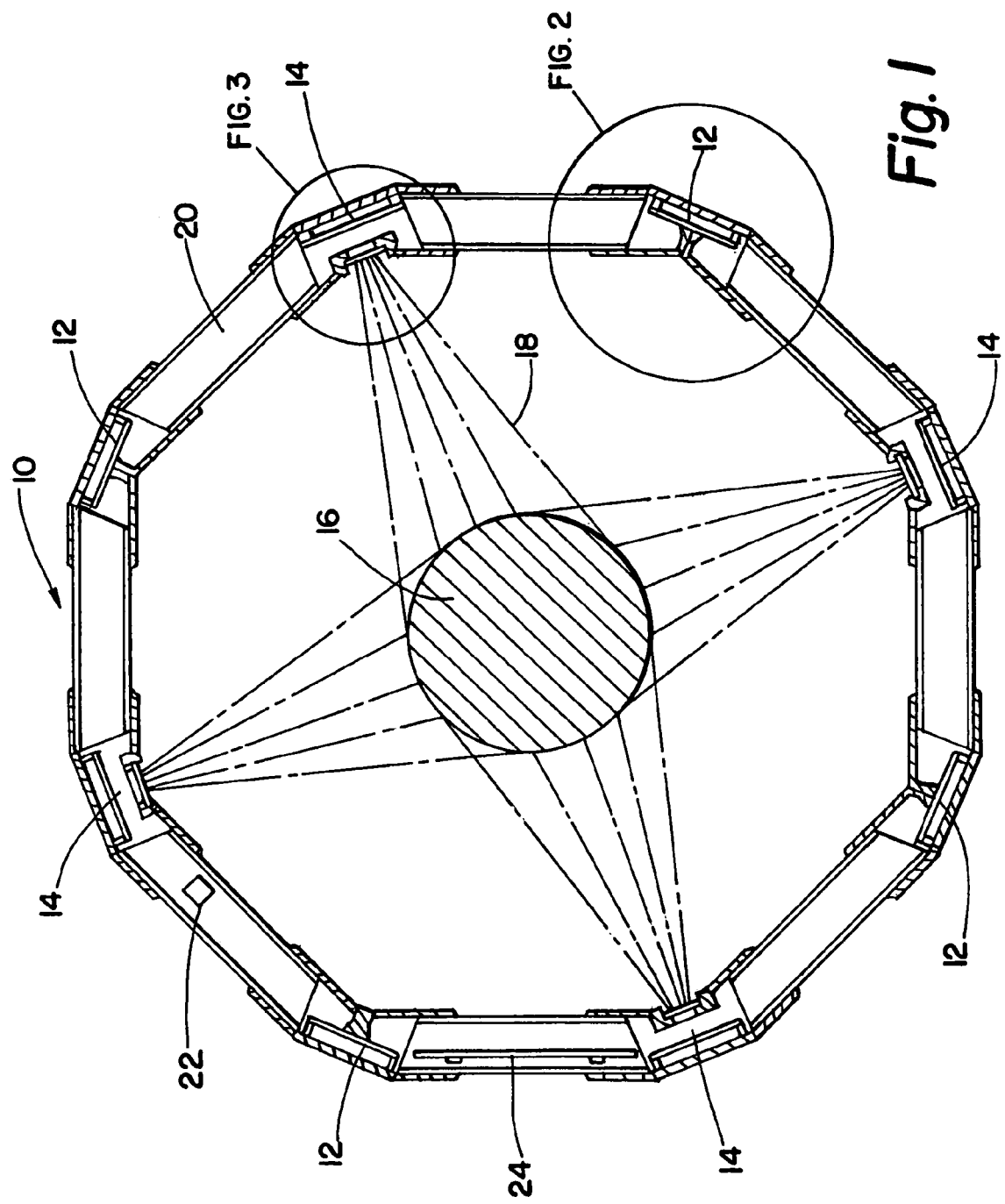

AMBIENT LIGHT

EAST-LIT

NORTH-LIT

EAST DELTA

NORTH DELTA

BOTH

INTERSECTION

APPARATUS FOR DETERMINING A THREE DIMENSIONAL SHAPE OF AN OBJECT

This application claims the benefit of U.S. Provisional Application No. 60/611,364, filed on Sep. 18, 2004 which is expressly incorporated herein.

BACKGROUND OF THE INVENTION

The present invention relates generally to the capturing of three dimensional data of the shape of an object, and more particularly involves the use of cameras (or imagers) and light projectors to capture images of an object and storing that data for processing into a three-dimensional model of the shape of the object. In a preferred embodiment the invention is useful in fitting amputees with properly fitted prosthetic devices.

It is known to sense the shape of body parts or limbs three-dimensionally by means of active laser scanners. See, for example, PCT Publication WO92/08175. It is also known to use photogrammetric systems employing passive stereo cameras and thin, tight fitting envelopes of material carrying a high contrast pattern worn over the body part being sensed. See, for example, U.S. Pat. No. 5,911,126.

The present invention employs light projectors preferably mounted on or in a structure which is preferably in the shape of a ring, and cameras preferably mounted on or in the ring. The structure is placed over the object to be sensed and light planes are projected onto the object. The cameras and projectors are preferably electronically controlled to operate in a predetermined sequence to capture images of the light planes projected onto the object.

The structure is preferably connected to a computer and display. A processor analyzes the data captured to create a three-dimensional model of the object. To create the 3D model the invention preferably uses data taken from the two-dimensional edges of the light planes on the object from the cameras positioned at various angles to the object and converts the data to a 3D model.

In one preferred embodiment the 3D data model may be used in the manufacture of properly fitted prosthetic devices for an amputee. A prosthetist may operate the mobile apparatus of the present invention wherever the amputee may happen to be located. Data collected from the use of the apparatus of the present invention may be stored in a computer used by the prosthetist. Later the prosthetist may download the data stored on an amputee to be used in the manufacture of a properly fitted prosthetic device for the amputee.

Properly fitting an amputee with a prosthetic device is important to the comfort and health of the amputee as well as to the usefulness of the prosthetic device. An improperly fitted prosthetic device can cause discomfort to the amputee, and can cause sores or blisters to develop on or near the amputee's stump. By mapping the various contours of an amputee's stump in a three-dimensional data model that can later be downloaded, a manufacturer of prosthetic devices can produce a better fitting prosthetic device for the amputee that recognizes and accommodates substantially the same contours of the amputee's stump.

The present invention may be used directly on an amputee's stump or in association with a covering or liner worn over the stump. There are very few limits on the use of the present invention. It is really only limited in its use by the size of the structure and the object being sensed. The object needs to be able to fit in the structure about which the cameras and projectors are arranged.

BRIEF DESCRIPTION OF THE DRAWINGS

FIG. 1 shows a plan view of a preferred embodiment of the apparatus of the present invention;

DETAILED DESCRIPTION OF PREFERRED EMBODIMENT(S)

Figure 3:
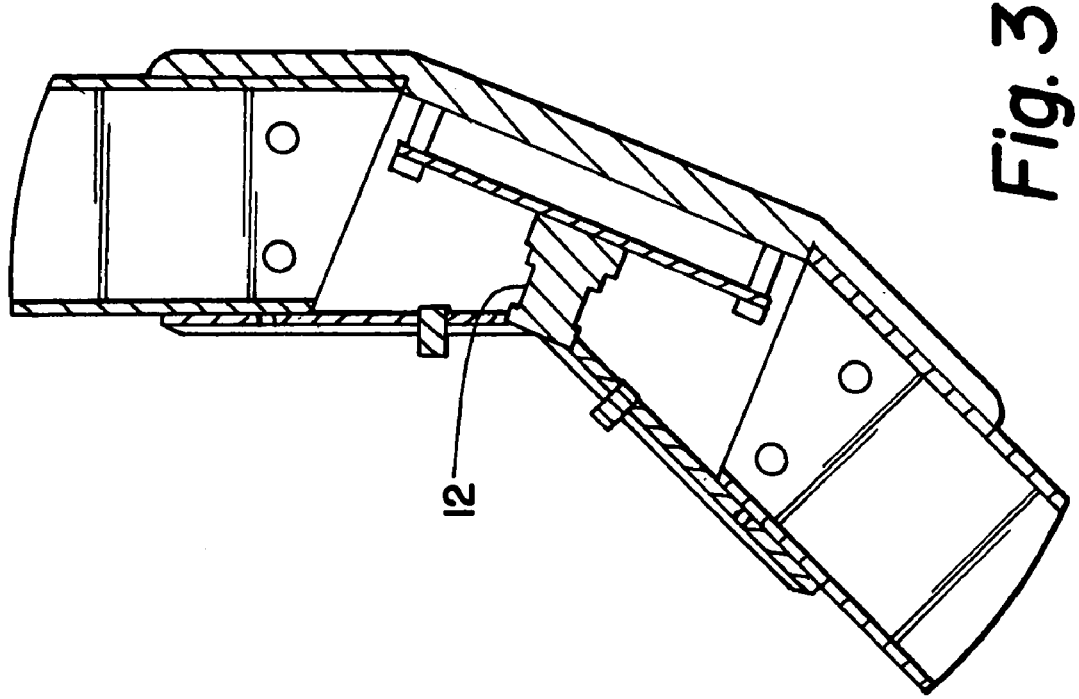
FIG. 3 shows a cross section view taken along section D of FIG. 1.
Figure 2:
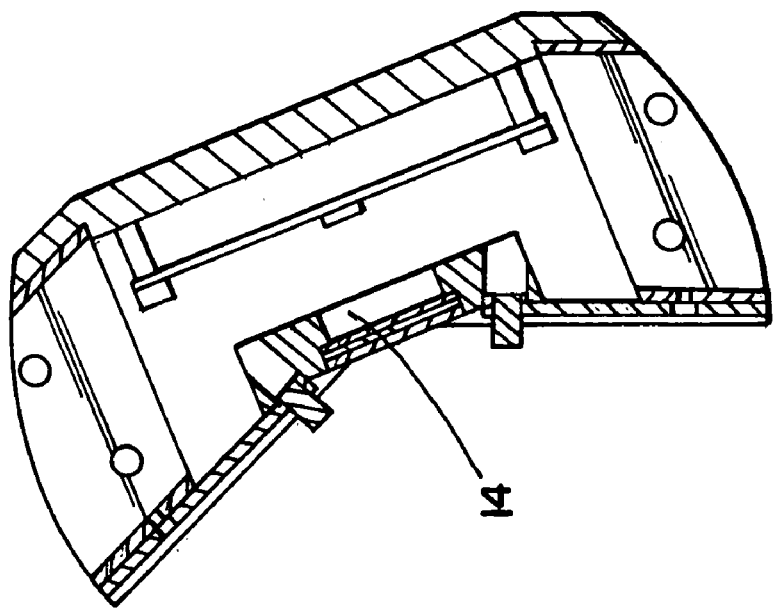
FIG. 2 shows a cross section view taken along section F of FIG. 1.
Figure 4A:
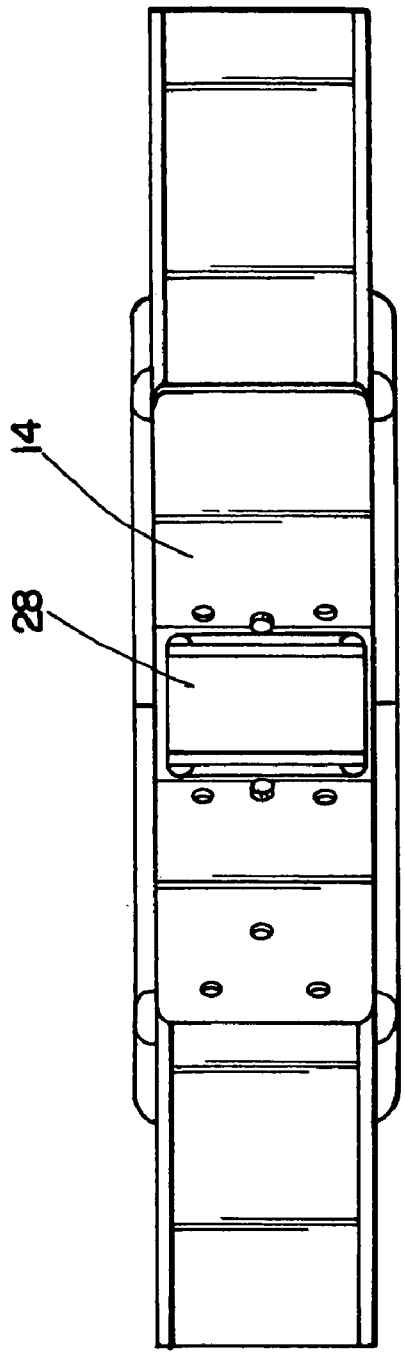
FIGS. 4A (with a light pattern filter in place) and 4B (with LEDs visible) show two modes of the projector device shown in cross section view taken from FIG. 2.
Figure 4B:
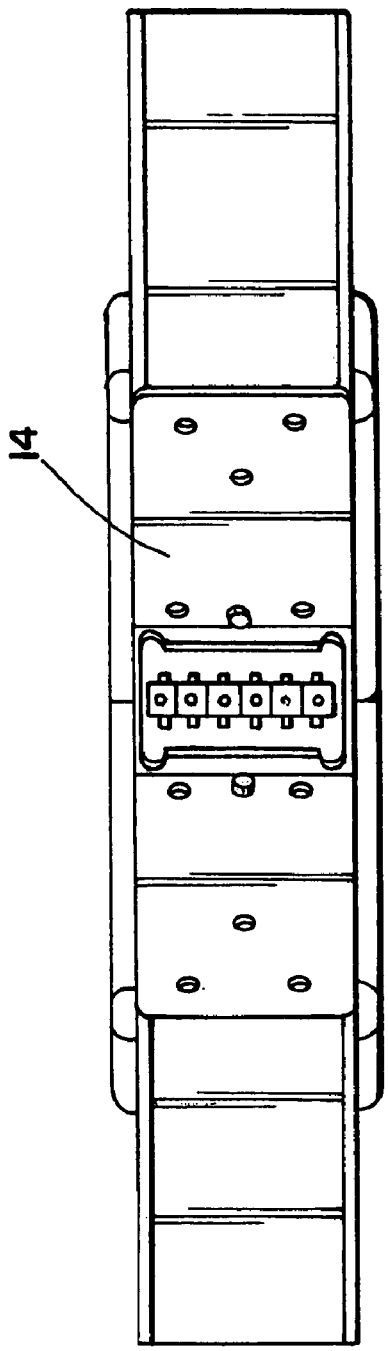
Figure 5:
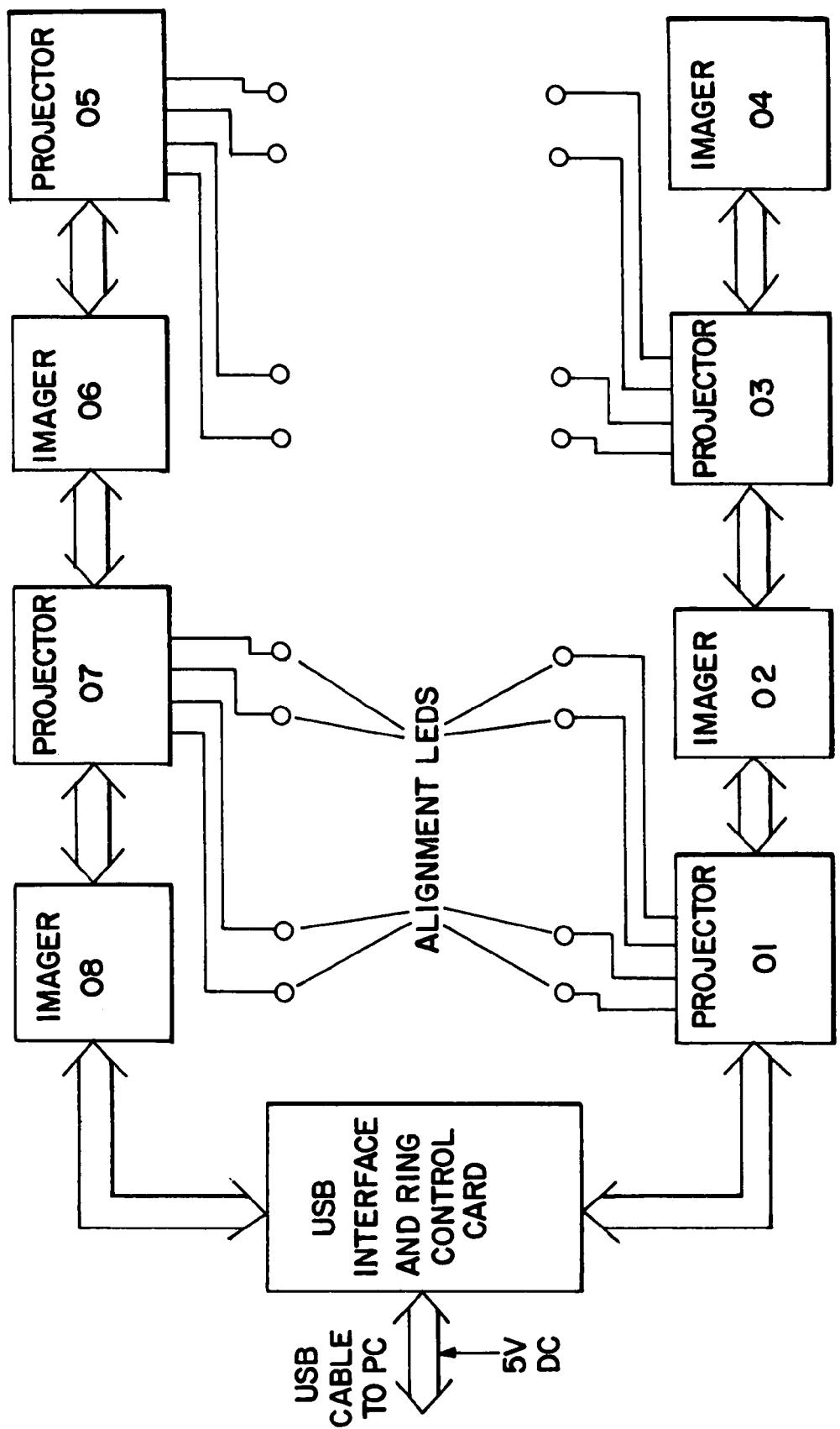
FIG. 5 shows a high level block diagram of a preferred embodiment of the apparatus of the present invention, including projectors and imagers.
Figure 6A:
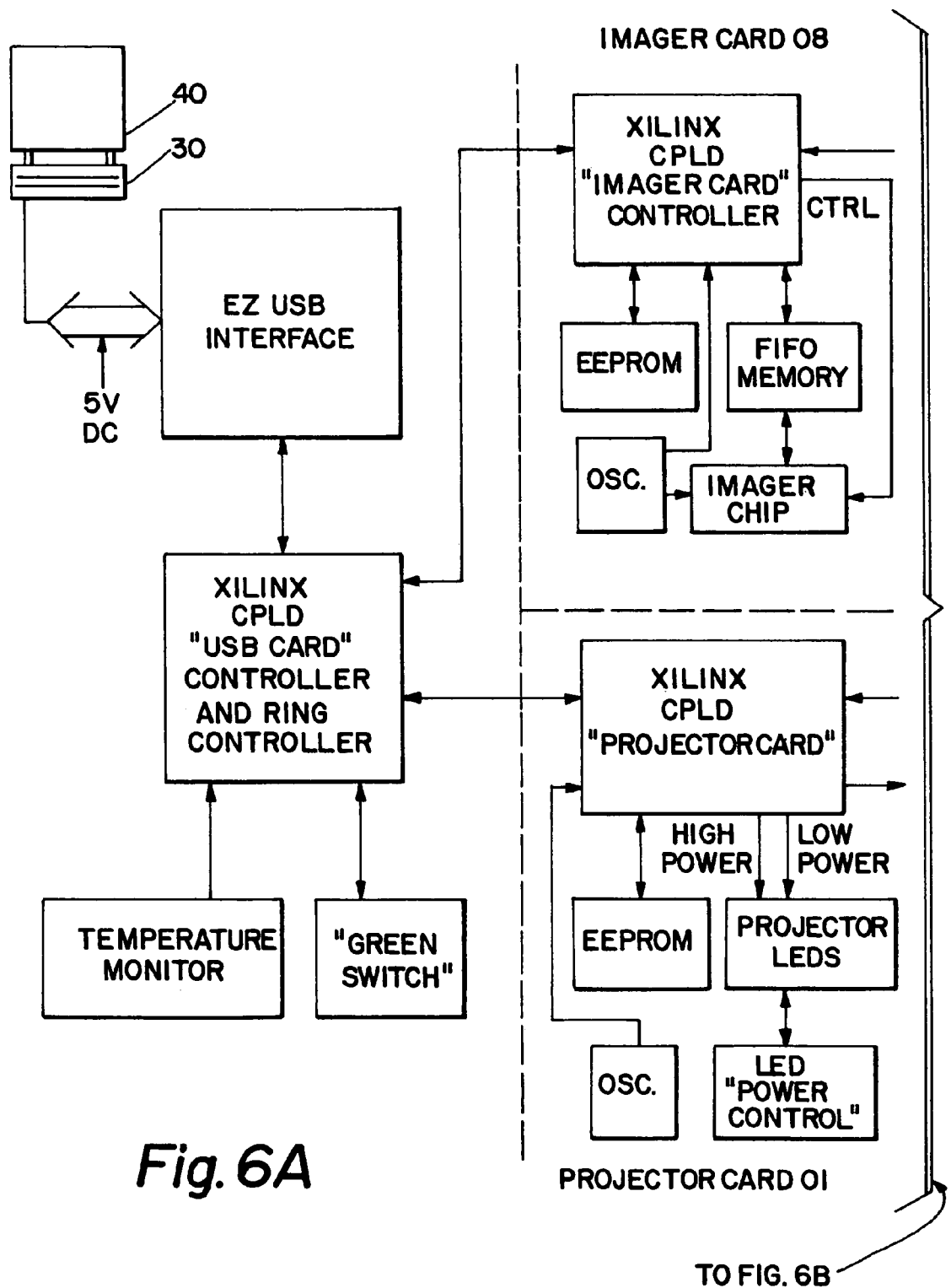
FIG. 6 shows a more detailed block diagram of a portion of the preferred embodiment of the apparatus shown in block diagram form in FIG. 5.
Figure 6B:
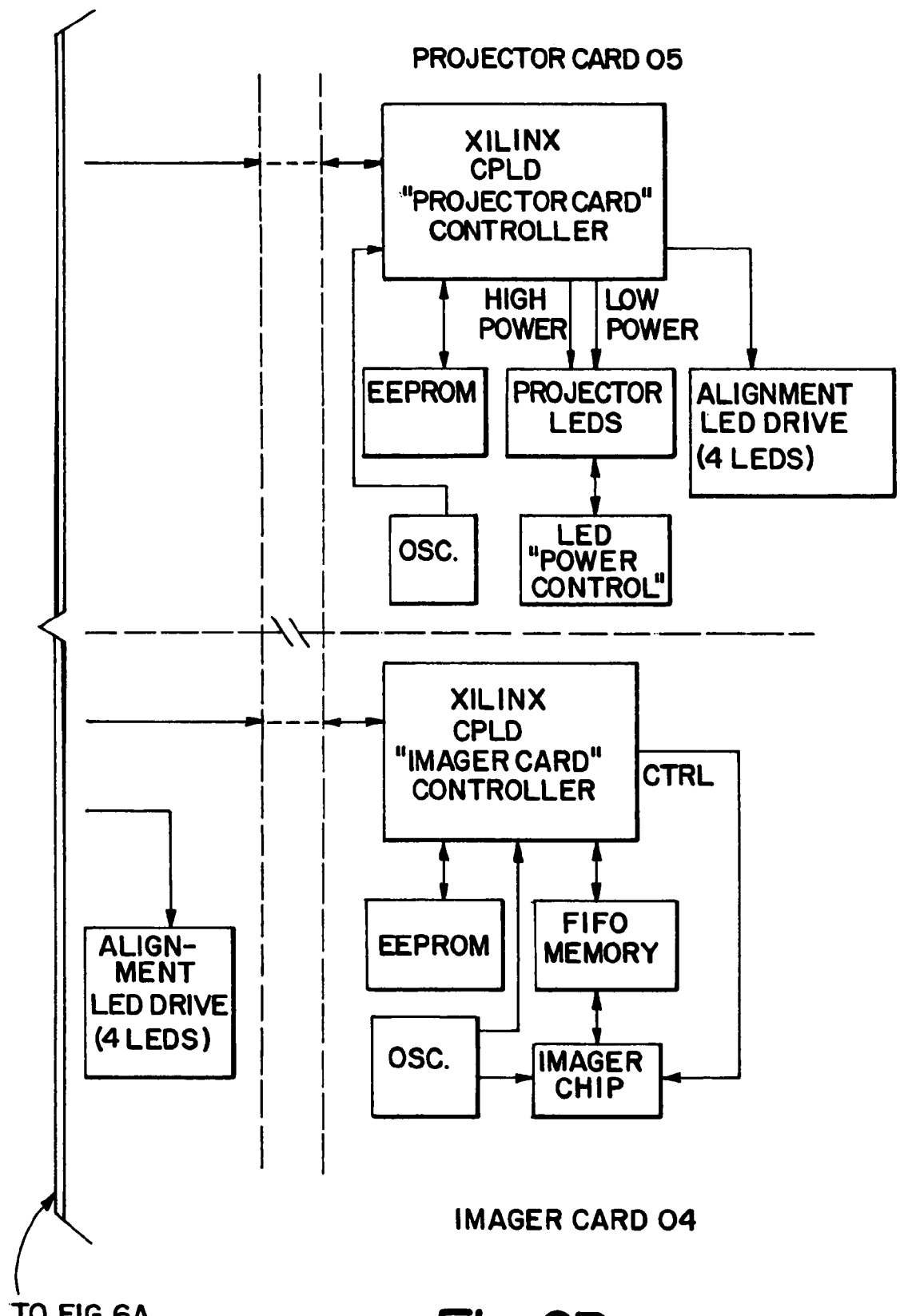
Figure 7:
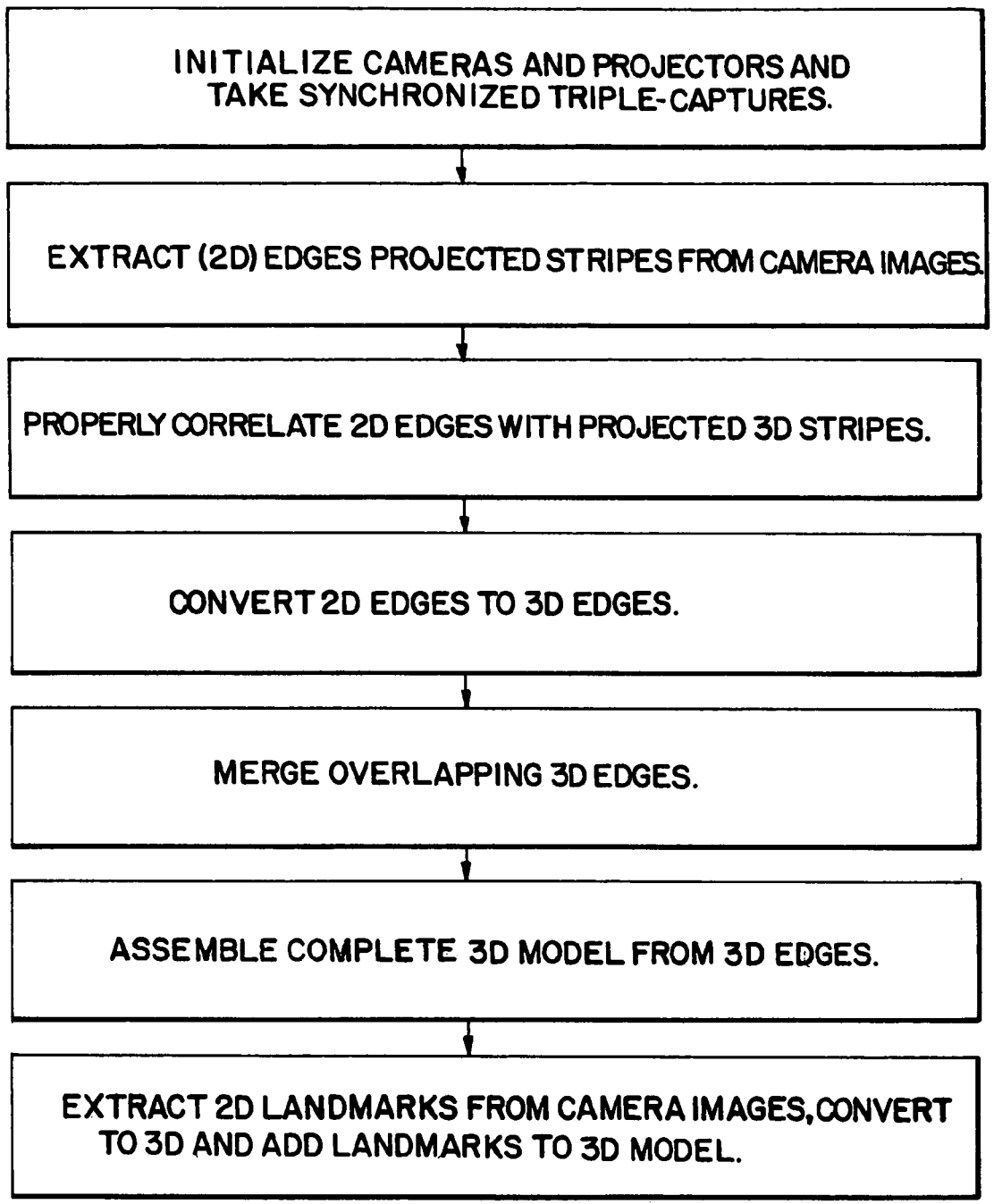
FIG. 7 shows a flow diagram of the operation of 3D data modeling of the present invention.

With reference to the figures, there is shown in FIG. 1 a preferred embodiment of the apparatus 10 of the present invention. It comprises a ring structure 20 having a plurality of cameras 12 and projectors 14. The ring structure 20 is placed around an object 16 to be sensed or measured. Light planes 18 from the projectors 14 are aimed at the object 16 and the cameras 12 are actuated to gather and store digital images of the object 16 having the light planes projected thereon. Since the cameras 12 are taking images from several angles around the object 16 data is collected from practically all directions around the object. The data collected by the cameras 12 may be stored in a database associated with the ring structure itself or connected to the ring structure. A personal computer (PC) 30 may be electronically connected 22 to the ring structure 20 to analyze the data and display 40 a 3D image of the object. The object may be practically any object able to be placed inside the dimensions of the ring.

In one embodiment of the present invention the object 16 is a stump of an amputee. A prosthetist may operate the ring structure to gather data to form a 3D model of the amputee's stump. The data collected may be used in the manufacture of a prosthetic device for the amputee. The stump may be covered in advance of the image gathering by a gel liner common to the industry of prosthetics, or by other covering means.

The present invention is preferably comprised of cameras, projectors, and a ring structure. There are preferably four cameras built into the structure. On a target object placed at the center of the ring, each camera is preferably able to 'see' approximately 10" up, 10" down, and 7" from side to side. The cameras should be focused for the proper exposure and synchronized for operation. There are preferably four projectors built into the structure. Each projector is preferably able to project 21 planes of light in towards the center of the ring.

The planes of light are preferably evenly spaced and preferably fan out in an evenly spaced manner. For a model approximately 4" in diameter, the projected planes of light will preferably illuminate a 20" range (10" up and 10" down) of the model. Due to the high amount of current necessary to flash a projector, a large capacitor is preferably mounted on the projector card and fully charged before initiating a flash. The inside (working) surface of the ring is preferably approximately 25" in diameter. The ring preferably houses, as noted above, four cameras and four projectors evenly spaced in an alternating sequence around the ring. Each camera and projector is preferably connected, in a daisy-chain arrangement, to a USB/processor board 24 inside the structure, which ultimately controls the cameras and projectors based upon commands sent over a USB channel from the user's PC.

The projector and camera arrangement, and usage are preferably as follows: The four projectors may be arranged in global orientation and designated North, South, East, and West. The four cameras may be arranged between the projectors and designated Northeast, Southeast, Northwest, and Southwest. While holding the structure normally, preferably using handgrips on the structure, the South projector is close to the operator's stomach, the East projector is close to the operator's right hand, the West is close to the operator's left hand, and the North is on the opposite side of the ring. The Northeast camera is between the North and East projectors, and so on.

Image capture is accomplished using the cameras. The cameras are preferably capable of taking a single full-frame (640×480) monochrome capture and sending it to the operator's PC. A capture can be issued for an individual camera or for all cameras simultaneously. The image data may be encrypted on the camera card itself and decoded on the user's PC.

For 3D capture and projector calibration purposes, the cameras are preferably capable of taking a 'triple capture'—three consecutive frames of video coordinated with the projectors in the following manner: the North and South projectors will be on during the first frame, no projectors will be on during the second frame, and the East and West projectors will be on during the third frame. Due to potential memory limitations on the camera cards, the cameras preferably only store every third row of pixels for each frame. As with the full-frame capture, a triple-capture may be issued for an individual camera or for all cameras simultaneously and the data may be encrypted for protection during data transfer.

Figure 8A:
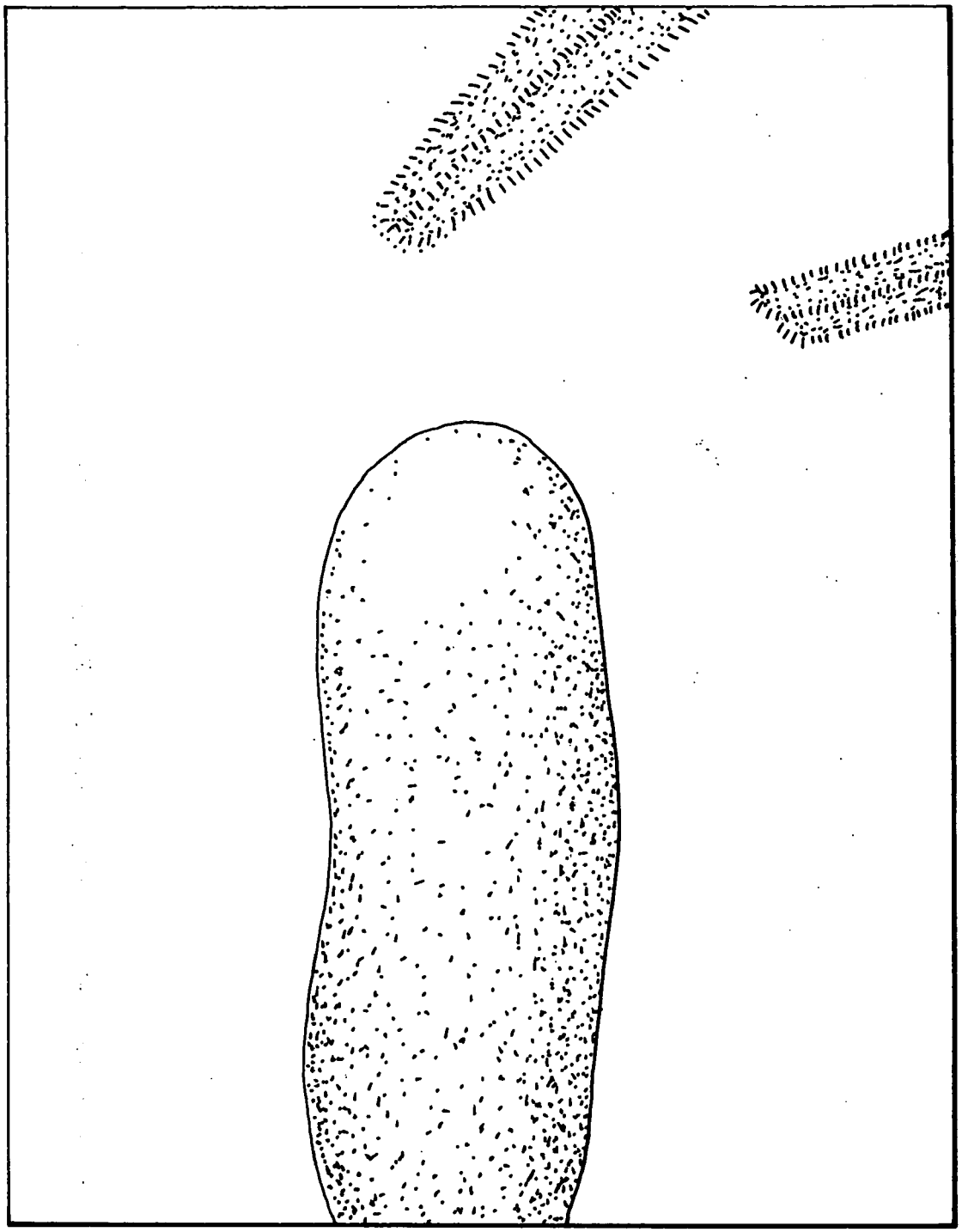
FIGS. 8(A), 8(B) and 8(C) show a sampling of processed frames using a single triple capture from the northeast camera.
Figure 8B:
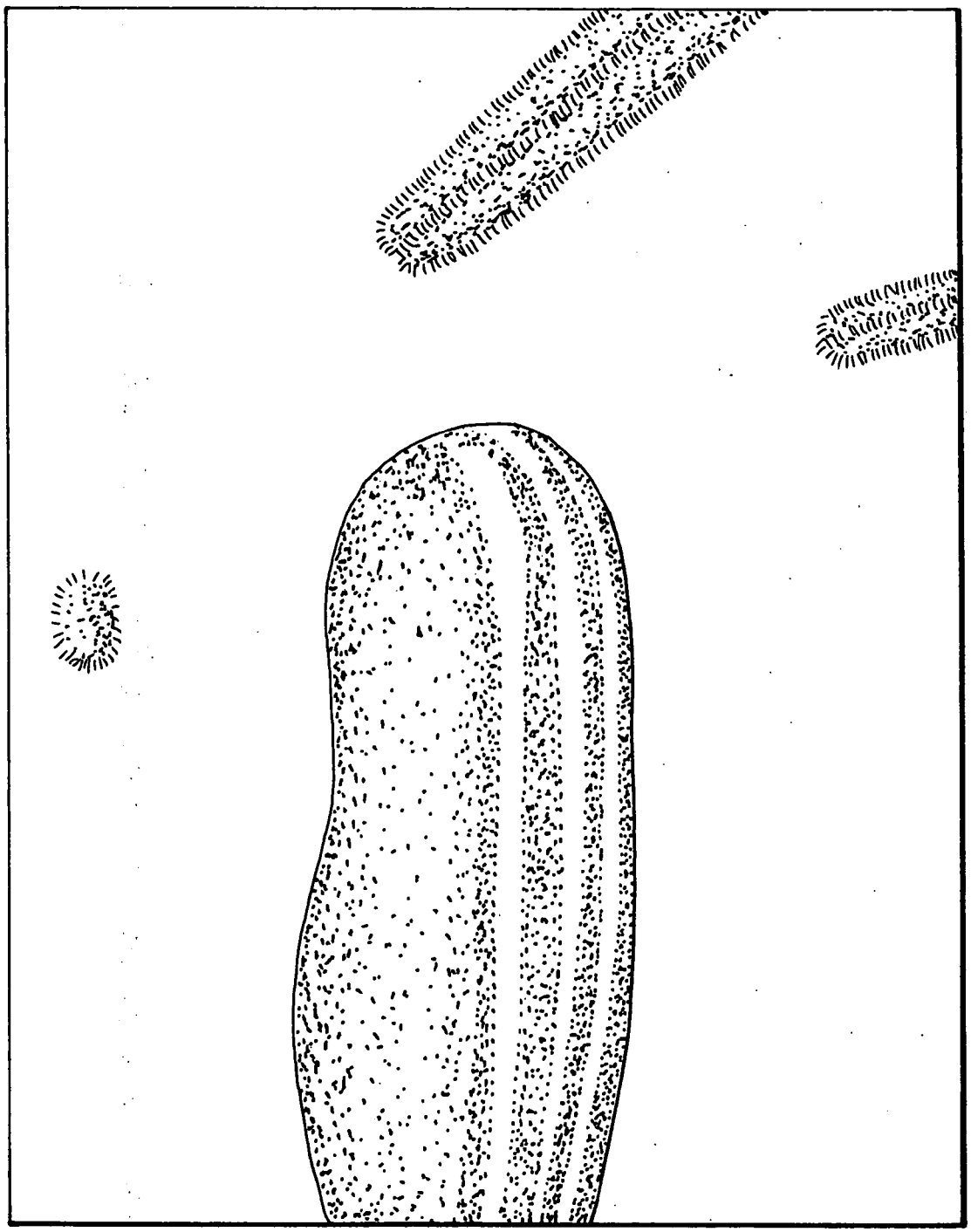
Figure 8C:
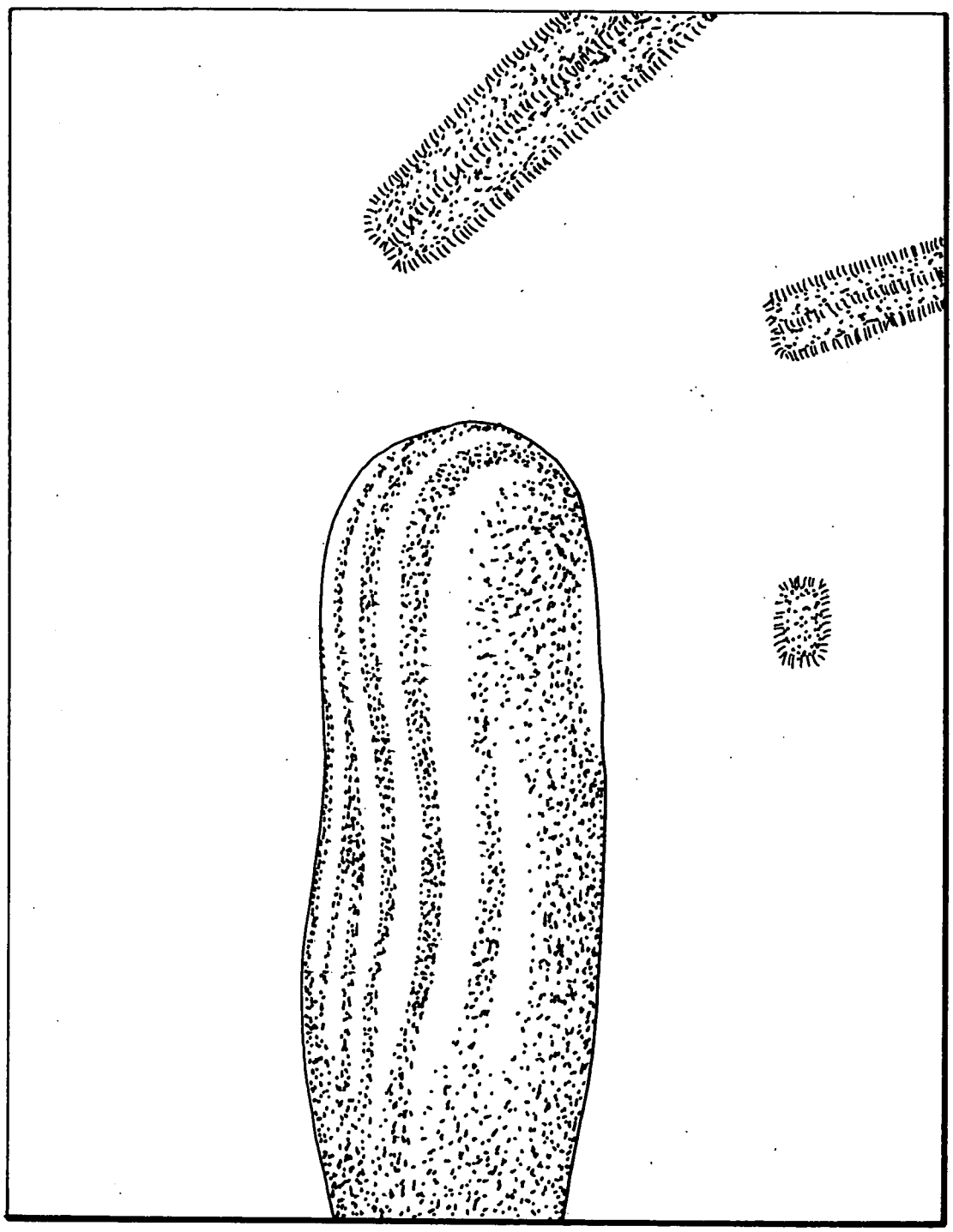

Once a triple capture is acquired, the software may process it in many ways. FIGS. 8A, 8B and 8C are a sampling of processed frames using a single triple capture from the northeast camera. The first three frames represent the raw data compressed into the triple capture.

Figure 9:
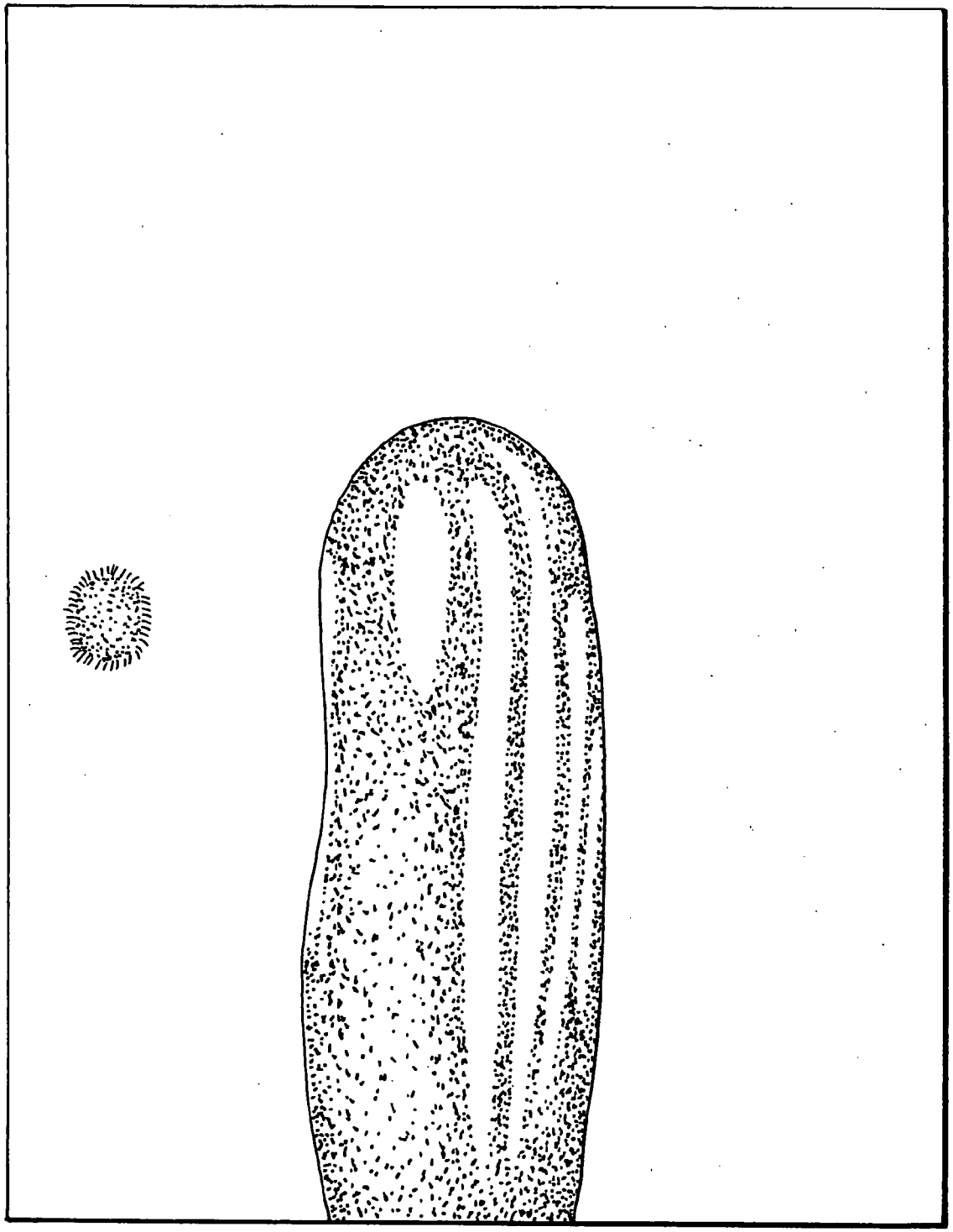
FIG. 9 or "East Delta" frame shows the subtraction of the ambient frame from the east-lit frame.

Post-Processed—The 'East Delta' frame or FIG. 9 subtracts the ambient frame from the east-lit frame. Notice that all of the background objects and even the lights in the room have been nullified. Also notice the bright light to the side of the model—this is the west projector firing.

Figure 10:
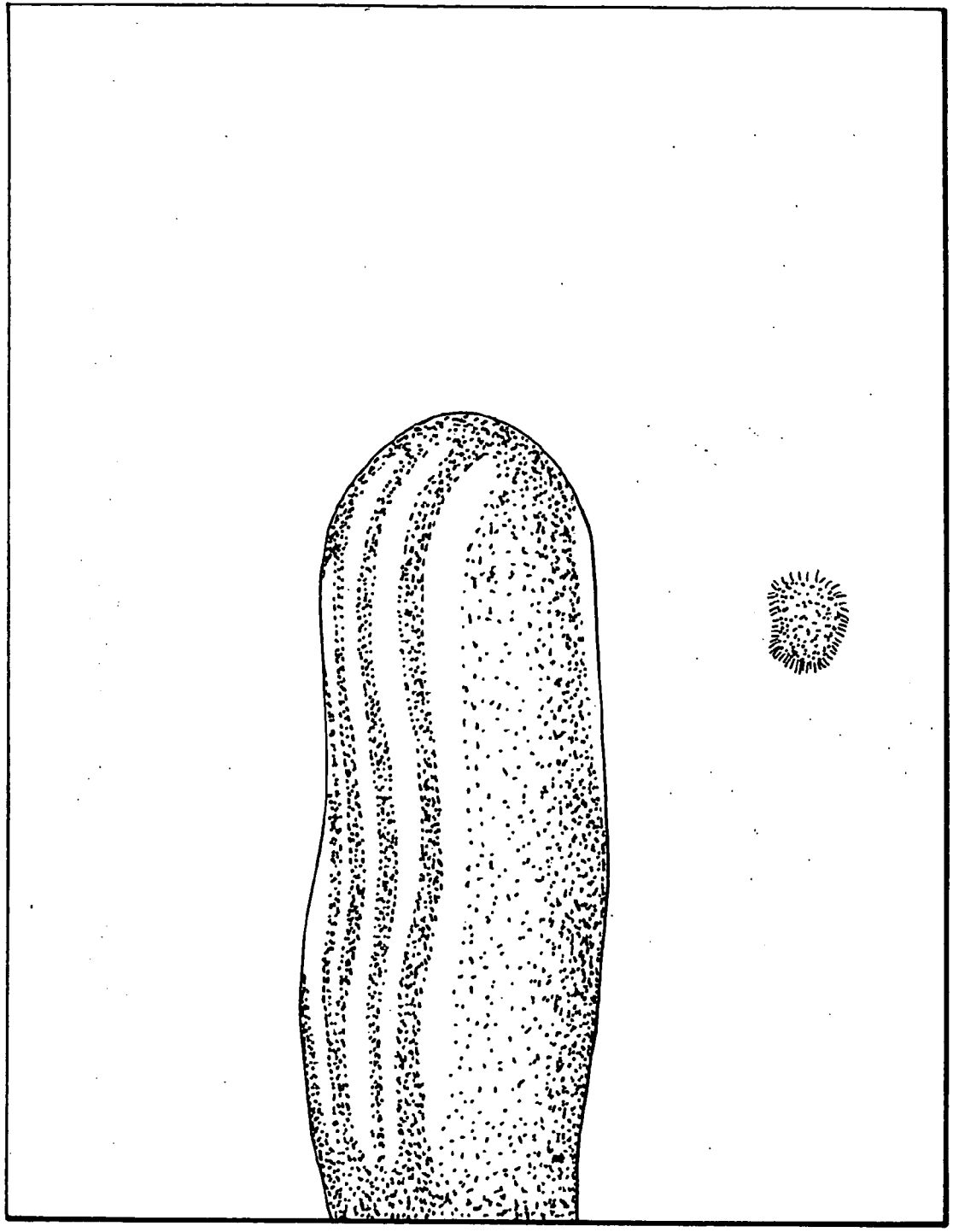
FIG. 10 or "North Delta" frame shows the subtraction of the ambient frame from the north-lit frame.

Post-Processed—The 'North Delta' frame or FIG. 10 subtracts the ambient frame from the north-lit frame. The bright light to the side of the model (object) is the south projector firing.

Figure 11:
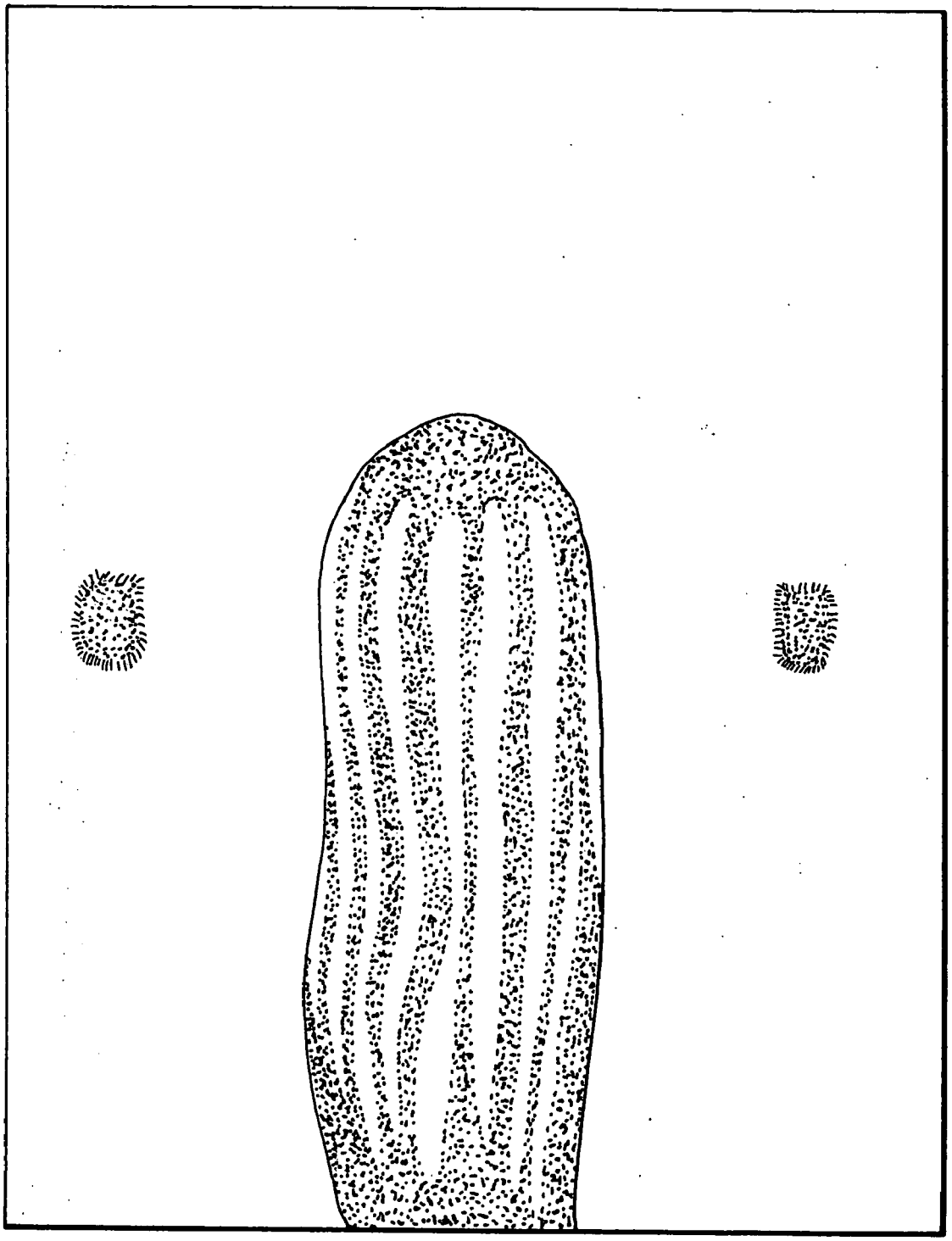
FIG. 11 or "Both" frame shows the addition of the two delta frames.

Post-Processed—The 'Both' frame or FIG. 11 is the addition of the two delta frames. It is used in diagnostics to confirm that the projected stripes are covering the model properly.

Figure 12:
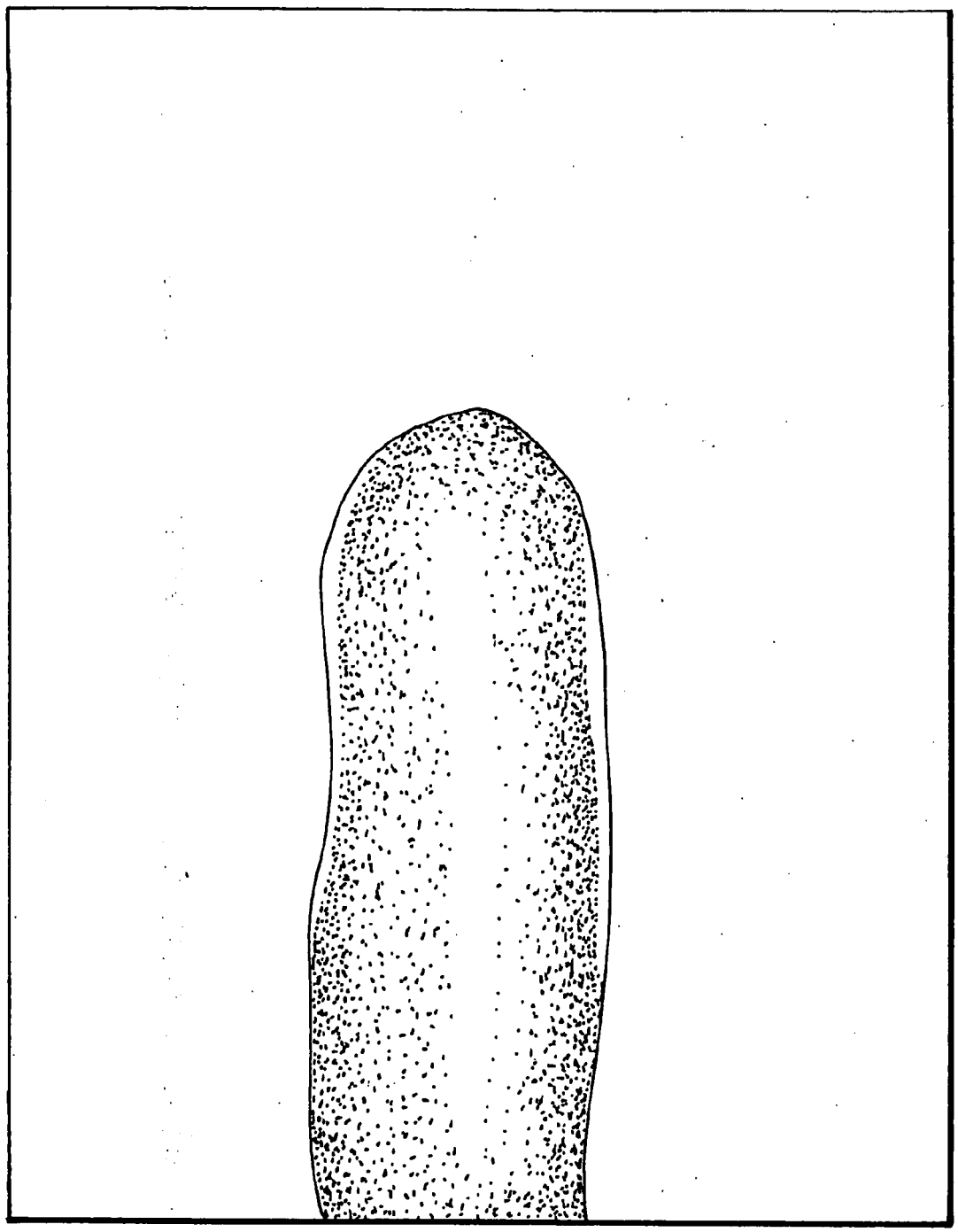
FIG. 12 or "Intersection" frame shows the light areas only when both delta frames are lit.

Post Processed—The 'Intersection' frame or FIG. 12 shows light areas only when both delta frames are lit. Notice that the bright light to the sides of the model are not visible in this view. To see why both edges of the model are lit, look at the North Delta frame. The right edge of the model gets lit by the North projector, and the left edge of the model gets lit by the South projector—on the far side of the ring. The same thing happens for the East Delta frame and the intersection of these two allows the extents of the model to be extracted.

Lens calibration preferably occurs once—during manufacturing—and it stores the characteristics of the individual lens into the EEPROM memory onboard the camera. A combination of the lens and field calibration allows the program to pair a camera pixel with an accurate three dimensional ray exiting the camera lens. Field calibration may be performed by the user at any time. It corrects for any shift or rotation of the camera card, or a slight deformation of the ring. This calibration uses a picture of the blue lights on the far side of the ring, as they are at a known physical position in space. A combination of the lens and field calibration allows the program to pair a camera pixel with an accurate three dimensional ray exiting the camera lens. Projector calibration may be performed by the user at any time. It determines the location of the planes of light being projected into the ring. This calibration correlates two delta frames from different cameras to determine the position of a calibration target held in front of the projector, normalizes the planes, and stores the result onboard the projector card. The projector calibration allows the program to know the precise mathematical formula of each three dimensional plane of light projected onto a model.

From a software perspective, capturing a 3D shape using the present invention preferably begins by connecting to the structure, loading the lens, field, and projector calibrations, setting up the cameras, and taking a triple capture on all four cameras simultaneously. At that point, having 12 pictures of the model (ambient/north-lit/east-lit from each of four cameras), and many other possibilities for post-processed images.

Once the captures are taken, there are six steps to create a model in the preferred embodiment:

1. Extract Edges from 2D Images. There are eight 'Delta frames' (Northeast camera—North-Lit, Northeast camera—East-Lit, Southeast camera—South-lit, etc). For each of these delta frames, identify the projected stripes, and extract the left and right edges of the each stripe. Because this data may be too close together (circumferentially) to be useful, average the right and left edges to create a single 'edge' for each stripe. In order not to extract stripes that may be in the background, this routine limits its 'filed of view' to the 2D extents of the model, found by examining the Intersection frame.
2. Correlate 2D Edges with 3D Planes. At this point, there are several edges extracted for each of the eight camera/projector pairs. This routine figures out which 2D edge corresponds to which 3D projected stripe. For instance, if there are three edges extracted for 'northeast-north-lit', the edges should correspond to projected 'north stripes' number 1/2/3, 2/3/4, . . . , or 18/19/20.
3. Convert Edges to 3D. Once knowing how each 2D (camera) edge corresponds to a 3D (projector) stripe, it is mathematically possible to convert to 3D edges. Find the intersection of a camera ray with a projector plane.
4. Merge Overlapping 3D Edges. If the same (projector) stripe is seen by two separate cameras, there will be presented two 3D edges that are identical (except that they may be slightly longer, shorter, etc). This section averages them together and feathers the edges.
5. Assemble the 3D Model. Using the post position and the array of 3D edges 'hanging in space', this routine builds a full Tracer model, smoothes, and completes the distal end and continues.

6. Extract and Add Landmarks to Model. Once the full model is built, this routine extracts dark dots from the ambient frames for each camera and projects any landmarks that are found onto the model.

The description herein of the preferred embodiment of the invention is for exemplary purposes and is not intended in any way to limit the scope of the allowed claims. The allowed claims are to be given their broadest interpretation under the law.

What is claimed is:

1. A system for formulating a three-dimensional data model of a shape of an amputee's stump in either a covered or uncovered condition, comprising:
   a structure generally in a shape of a ring, said ring of sufficient diameter to fit over and be spaced apart from the amputee's stump;
   four cameras secured to and in spaced arrangement about said structure, said cameras having lenses aimed at said stump;
   four light projectors secured to and in spaced arrangement about said structure, and in alternating arrangement with respect to said cameras, said projectors adapted to project light planes onto said stump;
   an actuator for initiating said cameras in a predetermined sequence to capture images of said light planes on said stump as at least one of said projectors project light planes onto said stump;
   a data storage device for storing data captured by said cameras;
   software for extracting two-dimensional edges of said captured light plane images from said stored data; and
   a data processor for processing said data so as to convert said two-dimensional edges to three-dimensional edges and to create therefrom a data model of the three-dimensional shape of said stump.

2. A system for formulating a three-dimensional data model of a shape of an amputee's stump in either a covered or uncovered condition, comprising:
   a structure generally in a shape of a ring, said ring of sufficient diameter to fit over and be spaced apart from the amputee's stump;
   a plurality of cameras secured to and in spaced arrangement about said structure, said cameras having lenses aimed at said stump;
   a plurality of light projectors secured to and in spaced arrangement about said structure, and in alternating arrangement with respect to said cameras, said projectors adapted to project light planes onto said stump;
   an actuator for initiating said cameras in a predetermined sequence to capture images of said light planes on said stump as at least one of said projectors project light planes onto said stump;
   a data storage device for storing data captured by said cameras;
   software for extracting two-dimensional edges of said captured light plane images from said stored data; and
   a data processor for processing said data so as to convert said two-dimensional edges to three-dimensional edges and to create therefrom a data model of the three-dimensional shape of said stump.

3. The system of claim 2, wherein the processor is housed within said structure.

4. The system of claim 2, further comprising a computer in communication with said processor to store data from said images.

5. The system of claim 2, further comprising a display device in communication with said processor, said display device adapted to display a visual image of the shape of said stump.

6. The system of claim 4, further comprising a display device in communication with said computer, said display device adapted to display an image of said stump.

7. The system of claim 2, wherein said object is a stump of a limb of an amputee and said data model is used in the manufacture of a properly fitted covering for said stump.

8. The system of claim 7, wherein said covering is a fitted sock.

9. The system of claim 7, wherein said covering is a fitted liner to be worn between an amputee's stump and a prosthetic device.

10. The system of claim 2, wherein four cameras and four projectors are installed around said structure.

11. The system of claim 2, wherein at least one camera captures an image and a computer in communication with said system stores said image capture.

12. The system of claim 2, wherein said cameras and said projectors are operated in a synchronized manner.

13. The system of claim 2, wherein said system is adapted to perform a triple capture for processing a three-dimensional data model of said stump.

* * * * *

(12) EX PARTE REEXAMINATION CERTIFICATE (8171st)
United States Patent
Pratt

(10) Number: US 7,447,558 C1
(45) Certificate Issued: Apr. 19, 2011

(54) APPARATUS FOR DETERMINING A THREE DIMENSIONAL SHAPE OF AN OBJECT

(75) Inventor: Gregory C. Pratt, Boca Raton, FL (US)

(73) Assignee: The Ohio Willow Wood Company, Mt. Sterling, OH (US)

Reexamination Request:
No. 90/009,434, May 14, 2009

Reexamination Certificate for:
Patent No.: 7,447,558
Issued: Nov. 4, 2008
Appl. No.: 11/228,697
Filed: Sep. 16, 2005

Related U.S. Application Data

(60) Provisional application No. 60/611,364, filed on Sep. 18, 2004.

(51) Int. Cl.
*G06F 19/00* (2006.01)
*G06K 9/00* (2006.01)

(52) U.S. Cl. .................. 700/118; 382/154; 600/587; 623/901

(58) Field of Classification Search .................. None
See application file for complete search history.

(56) References Cited

U.S. PATENT DOCUMENTS 4,302,097 A 11/1981 Chlestil

| | | |
|---|---|---|
| 4,645,348 A | 2/1987 | Dewar et al. |
| 5,432,703 A | 7/1995 | Clynch |
| 5,539,649 A | 7/1996 | Walsh et al. |
| 5,753,931 A | 5/1998 | Borchers et al. |
| 6,463,351 B1 | 10/2002 | Clynch |
| 7,162,322 B2 | 1/2007 | Arbogast et al. |
| 7,245,386 B2 | 7/2007 | Philipps et al. |
| 2005/0004472 A1 | 1/2005 | Pratt |
| 2005/0033140 A1 | 2/2005 | de la Rosa |

FOREIGN PATENT DOCUMENTS

DE 10328537 A1 6/2003
WO WO 2004/111571 A1 12/2004

*Primary Examiner* — B. James Peikari

(57) ABSTRACT

An apparatus is described that uses cameras arranged on, in, or about a structure adapted to fit over, around, or about an object to be measured. Projectors are arranged on, in, or about the structure to project light toward the object. The projectors and/or the cameras may be electronically connected to a computer processor which controls their operation. A light pattern is projected onto the object to be measured while the cameras capture images of the object from several angles about the object. The data collected from the images taken of the pattern on the object may be used to form a mathematical three-dimensional data model of the object. The three-dimensional model may be displayed in digital form on a visual display device of a personal computer. The three-dimensional model of the object may be used in the manufacture of fitments or coverings for the object. In one example, the apparatus is used by a prosthetist to map the stump of an amputee to properly fit the amputee with a prosthetic device.

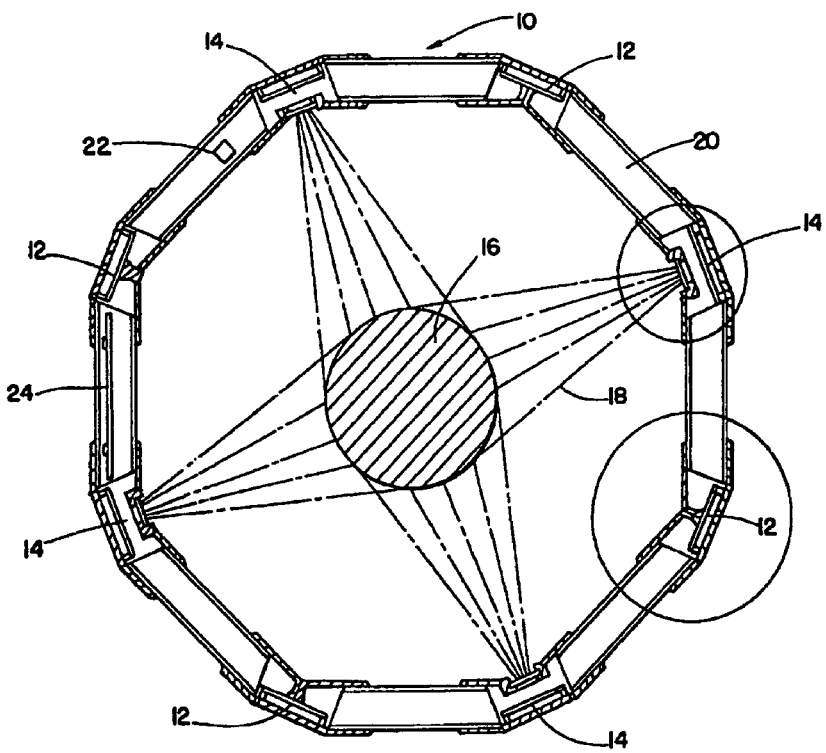

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 2, 8 and 9 are determined to be patentable as amended.

Claims 3-7 and 10-13, dependent on an amended claim, are determined to be patentable.

1. A system for formulating a three-dimensional data model of a shape of an amputee's stump in either a covered or uncovered condition, comprising:
   a structure generally in a shape of a ring, said ring of sufficient diameter to fit over and be spaced apart from the amputee's stump;
   four cameras secured to and in spaced arrangement about said structure, said cameras having lenses aimed at said stump;
   four light projectors secured to and in spaced arrangement about said structure, and in alternating arrangement with respect to said cameras, said projectors adapted to project light planes *in the form of spaced apart stripes* onto said stump;
   an actuator for initiating said cameras in a predetermined sequence to capture images of said light planes on said stump as at least one of said projectors project light planes onto said stump;
   a data storage device for storing data captured by said cameras;
   software for extracting two-dimensional edges of said captured light plane images from said stored data; and
   a data processor for processing said data so as to convert said two-dimensional edges to three-dimensional edges and to create therefrom a data model of the three-dimensional shape of said stump.

2. A system for formulating a three-dimensional data model of a shape of an amputee's stump in either a covered or uncovered condition, comprising:
   a structure generally in a shape of a ring, said ring of sufficient diameter to fit over and be spaced apart from the amputee's stump;
   a plurality of cameras secured to and in spaced arrangement about said structure, said cameras having lenses aimed at said stump;
   a plurality of light projectors secured to and in spaced arrangement about said structure, and in alternating arrangement with respect to said cameras, said projectors adapted to project light planes *in the form of spaced apart stripes* onto said stump;
   an actuator for initiating said cameras in a predetermined sequence to capture images of said light planes on said stump as at least one of said projectors project light planes onto sai stump;
   a data storage device for storing data captured by said cameras;
   software for extracting two-dimensional edges of said captured light plane images from said stored data; and
   a data processor for processing said data so as to convert said two-dimensional edges to three-dimensional edges and to create therefrom a data model of the three-dimensional shape of said stump.

8. The system of claim [7] *2*, wherein said [covering is a fitted sock] *light planes are evenly spaced*.

9. The system of claim [7] *1*, [wherein said covering is a fitted liner to be worn between an amputee's stump and a prosthetic device] *further comprising a light pattern filter on each of said plurality of light projectors, said light pattern filter allowing the light projector to which it is installed to project a plurality of light planes toward the center of said ring*.

* * * * *